United States Patent [19]

Uneme et al.

[11] Patent Number: 5,180,833

[45] Date of Patent: Jan. 19, 1993

[54] PROCESS FOR THE PREPARATION OF CHLOROTHIAZOLE DERIVATIVES

[75] Inventors: Hideki Uneme, Osaka; Noriko Higuchi, Matsubara; Isao Minamida, Kawabe, all of Japan

[73] Assignee: Takeda Chemical Industries, Ltd., Osaka, Japan

[21] Appl. No.: 666,128

[22] Filed: Mar. 7, 1991

[30] Foreign Application Priority Data

Mar. 16, 1990 [JP] Japan ................................ 2-67911

[51] Int. Cl.$^5$ .......................................... C07D 277/32
[52] U.S. Cl. ..................................... 548/202; 548/205
[58] Field of Search ............................... 548/202, 205

[56] References Cited

U.S. PATENT DOCUMENTS

| | | | |
|---|---|---|---|
| 4,742,060 | 5/1988 | Shiokawa et al. | 514/252 |
| 4,748,243 | 5/1988 | Beck | 548/202 |
| 4,845,106 | 7/1989 | Shiokawa et al. | 514/342 |

FOREIGN PATENT DOCUMENTS

| | | |
|---|---|---|
| 0260560 | 3/1988 | European Pat. Off. . |
| 0302389 | 2/1989 | European Pat. Off. . |
| 0366085 | 10/1989 | European Pat. Off. . |
| 0375907 | 11/1989 | European Pat. Off. . |
| 0376279 | 12/1989 | |
| 0381130 | 1/1990 | European Pat. Off. . |
| 0391205 | 3/1990 | European Pat. Off. . |

OTHER PUBLICATIONS

March, Advanced Organic Chemistry pp. 364–366 (1985).
Fieser Reagents for Organic Synthesis p. 428 (1987).
Potts, Comprehensive Heterocyclic Chemistry, vol. 6, pp. 295, 6, 311 (1984).
G. J. Durant et al., Cyanoguanidine–Thiourea Equivalence in the Development of the Histamine H2-Receptor Antagonist, Cimetidine, Journal of Medicinal Chemistry (1977), vol. 20, No. 7, 901–906.

*Primary Examiner*—Robert Gerstl
*Attorney, Agent, or Firm*—Wegner, Cantor, Mueller & Player

[57] ABSTRACT

Novel processes for preparing 2-chlorothiazoles, useful as an intermediate for insecticides, from allyl isothiocyanate derivatives having the formula [II]:

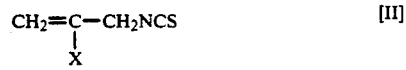

wherein X represents a leaving group, are simple and convenient reaction procedures under mild conditions without need of a large excess of a chlorinating agent. Further, processes for preparing 5-(aminomethyl)-2-chlorothiazole or salts thereof from the compound [II] achieve higher yields by simple, convenient and inexpensive procedures.

11 Claims, No Drawings

PROCESS FOR THE PREPARATION OF CHLOROTHIAZOLE DERIVATIVES

FIELD OF THE INVENTION

The present invention relates to a novel process for preparing 2-chlorothiazole compounds which are useful as intermediates for insecticides.

BACKGROUND OF THE INVENTION

It was disclosed in European Patent Application Laid Open No. 192,060 and Japanese Patent Application Laid Open No. 171/1990 that 2-chloro-5-(chloromethyl)thiazole of the formula

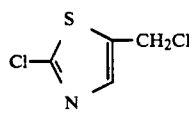

(optionally called compound [I] hereinbelow) and 5-(aminomethyl)-2-chlorothiazole of the formula

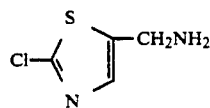

(optionally called compound [III] hereinbelow) or salts thereof are useful as an intermediate for insecticides. There is, however, only a specific process disclosed in Japanese Patent Application Laid Open No. 83979/1988 for preparing compound [I] in which allyl isothiocyanate is reacted with a chlorinating agent as illustrated below.

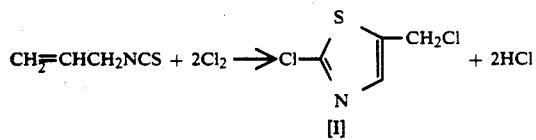

This process needs a large excess of the chlorinating agent, high temperature and furthermore involves a very vigorous reaction. Consequently, a plurality of by-products is formed in addition to merely a small amount of the desired compound [I] in the reaction, and separation thereof from the by-products is troublesome. Thus the isolated yield of compound [I] results in quite low. The process therefore can by no means be considered as a good process for preparing compound [I].

Japanese Patent Application Laid Open No. 171/1990 also discloses a process comprising reaction of compound [I] with potassium phthalimide as a process for preparing compound [III]. However, a simpler, less costly and higher yield process is desired.

Such being the case, it is an object of the invention to provide a process for preparing 2-chloro-5-(chloromethyl) thiazole (compound [I]) from an allyl isothiocyanate derivative represented by the formula [II] shown below (optionally called compound [II] hereinbelow) by simple and convenient reaction procedures under mild conditions without need of a large excess of a chlorinating agent, a process for preparing 5-(aminomethyl)-2-chlorothiazole [III] or salts thereof from compound [II] via compound [I] and a novel process for preparing compound [III] or salts thereof in a higher yield by simple, convenient and inexpensive procedures.

SUMMARY OF THE INVENTION

Extensive studies were made by us on the process for preparing compound [I] and compound [III] or salts thereof in order to achieve the above-mentioned object. As a result of these studies, we have discovered that compound [I] of a high purity can be produced in a high yield through very simple reaction procedures and aftertreatments by reacting an allyl isothiocyanate derivative represented by the formula

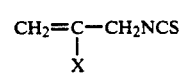

wherein X represents a leaving group with a chlorinating agent under mild conditions, unexpectedly without need of using a large excess of the chlorinating agent, that compound [III] or salts thereof can be produced by aminating the compound [I] thus prepared from compound [II] and that the compound [III] or salts thereof can be produced unexpectedly in a high yield by reacting the compound [I] with liquid ammonia or hexamethylenediamine. The present invention has been completed on the basis of these discoveries.

Thus the invention relates to (1) a process for preparing 2-chloro-5-(chloromethyl)thiazole (compound [I]) which comprises reacting compound [II] with a chlorinating agent, (2) a process for preparing 5-(aminomethyl)-2-chlorothiazole (compound [III]) or salts thereof which comprises reacting compound [II] with a chlorinating agent to give 2-chloro-5-(chloromethyl)thiazole (compound [I]) and then reacting the compound [I] thus obtained with an aminating agent, and (3) a process for preparing 5-(aminomethyl)-2-chlorothiazole (compound [III]) or salts thereof which comprises reacting compound [I] with liquid ammonia or hexamethylenetetramine.

These processes are excellently simple and advantageously useful on an industrial scale in the preparation of insecticides and other valuable compounds.

DETAILED DESCRIPTION OF THE INVENTION

According to the invention, there are provided processes for preparing 2-chloro-5-(chloromethyl)thiazole (compound [I]) which comprises reacting the compound [II] with a chlorinating agent. The compound [I] which is excellently useful in synthesizing insecticides is selectively produced in an unexpected high yield.

The compound [I] thus produced can be converted into the compound [III] advantageously.

Another aspect of the invention provides processes for preparing 5-(aminomethyl)-2-chlorothiazole ([III]) or salts thereof which comprises reacting compound [II] with a chlorinating agent followed by the reaction of the compound [I] thus obtained with an aminating agent, or compound [I] with liquid ammonia or hexamethylenetetramine.

As the leaving group defined by X in the above formula is used, for example, halogen such as fluorine, chlorine, bromine or iodine; $C_{1-4}$ alkylsulfonyloxy optionally substituted with 1–3 halogen atoms (such as Cl, Br or F) such as methanesulfonyloxy, ethanesulfonyloxy, butanesulfonyloxy or trifluoromethanesulfonyloxy; $C_{6-10}$ arylsulfonyloxy optionally substituted with 1-4 lower alkyl groups (e.g. methyl or ethyl) or halogen atoms (e.g. Cl, Br or F) such as benzenesulfonyoxy, p-toluenesulfonyloxy, p-bromobenzenesulfonyloxy or mesitylenesulfonyloxy; $C_{1-6}$ acyloxy optionally substituted with 1-3 halogen atoms (such as Cl, Br or F) such as acetyloxy, propionyloxy or trifluoroacetyloxy or $C_{6-10}$ arylcarbonyloxy such as benzoyloxy. Usually, the compound [II] wherein X is chlorine (2-chloroallyl isothiocyanate) is most readily available.

The "chlorinating agent" represents chlorine and compounds releasing chlorine under reaction conditions such as sulfuryl chloride. The "aminating agent" represents ammonia (intended in the invention to include aqueous ammonia) and compounds in which ammonia is protected to prevent polyalkylation, for example, dicarboximides such as phthalimide and succinimide, sulfonamides such as p-toluenesulfonamide and trifluoromethanesulfonamide, carboxamides such as acetamide and trifluoroacetamide, carbamic acid esters such as tert-butyl carbamate and methyl carbamate, hexamethylenetetramine and trichloroamine. Additionally, if feasible, alkali metal salts of these compounds such as potassium amide, sodium amide, potassium phthalimide and sodium phthalimide are included. The protective group is removed by a known method except for the cases where ammonia or an alkali metal salt thereof is used as the aminating agent. It is especially preferred to use liquid ammonia, aqueous ammonia, potassium phthalimide, sodium phthalimide and hexamethylenetetramine as the aminating agent.

Examples of the salts of 5-(aminomethyl)-2-chlorothiazole, namely, compound [III] include the salt with an inorganic acid such as hydrochloric, hydrobromic, hydroiodic, phosphoric, sulfuric or perchloric acid, or with an organic acid such as formic, acetic, tartaric, malic, citric, oxalic, succinic, benzoic, picric, methanesulfonic or p-toluenesulfonic acid.

The process of the invention can be carried out, for example, under reaction conditions as described below.

(A) 2-Chloro-5-(chloromethyl)thiazole (compound [I]) can be prepared by reacting an allyl isothiocyanate derivative [II] with a chlorinating agent.

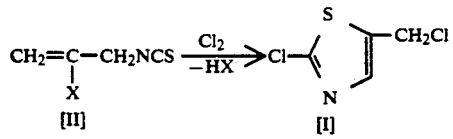

The reaction may be carried out in the absence of solvent. It may also be done following dilution with a solvent that is inert under reaction conditions. As the solvent are preferred, for example, halogenated hydrocarbons such as dichloromethane, chloroform, carbon tetrachloride, 1,2-dichloroethane, 1,1,1-trichloroethane and 1,1,2,2-tetrachloroethane.

The chlorinating agent is used usually in an amount of 1-1.5 equivalents on the basis of the allyl isothiocyante derivative [II], but an excess amount (2-10 equivalents) may also be used as required. When chlorine is used as a chlorinating agent, gaseous chlorine may directly be introduced into the reaction system, or a solution in an appropriate solvent (such as chloroform or carbon tetrachloride) may be employed.

The reaction may be carried out at a temperature between −20° C. and 150° C. A temperature between 0° C. and 60° C. is especially preferred.

It is believed that the reaction proceeds via a mechanism shown below.

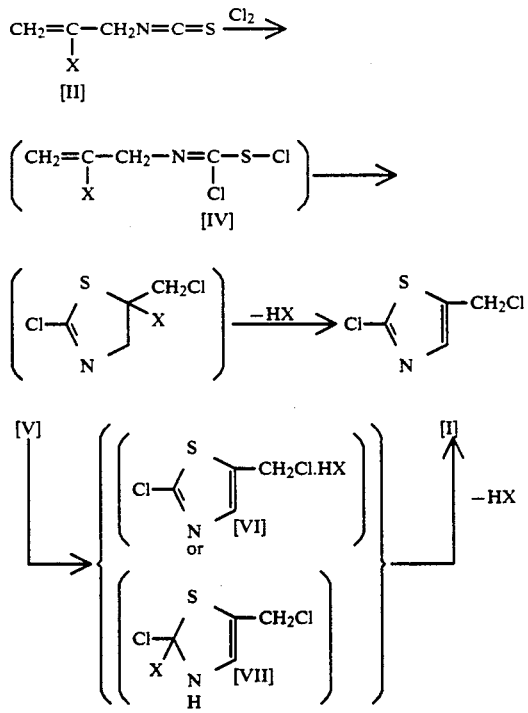

wherein X represents a leaving group as stated above.

Thus, chlorine is added to an allyl isothiocyanate derivative [II] to form a sulfenyl chloride derivative [IV] (called compound [IV] hereinbelow). Compound [IV] is then subjected to cyclization addition to give a 2-thiazoline derivative represented by the formula [V] (called compound [V]). Compound [V] in turn releases HX spontaneously or by heating or with a base to be converted to 2-chloro-5-(chloromethyl)thiazole (compound [I]). In some cases, HX salt of compound [I] (called compound [VI]) or HX adduct of of compound [I] (called compound [VII]) is formed as an intermediate at this atage.

The reaction, if conducted at a low temperature or in diluted solution, tends to terminate upon formation of compound [IV] or compound [V], but if conducted at a high temperature and in the absence of solvent or in concentrated solution, tends to proceed until the desired 2-chloro-5-(chloromethyl)thiazole ([I]) is formed. Therefore, compound [I] may be prepared either by first carrying out the reaction at a low temperature or in diluted solution to produce compound [IV] or [V] as the main product and then raising the reaction temperature or concentrating, or doing both to produce compound [I], or by carrying out the reaction at a high temperature and in the absence of solvent or in concentrated solution from the beginning to produce compound [I]. The "low temperature", "high temperature", "diluted solution" and "concentrated solution" herein referred to are variable depending upon such factors as nature of the chlorinating agent, scale of the reaction and reaction time and cannot be specified. Usually, however, the "low temperature" represents a temperature between −20°–20° C., the "high temperature" a temperature between 30°–100° C., the "diluted solution" a solution in a concentration of about 20% or below, and the "concentrated solution" a solution in a concentration of about 40% or above.

In some cases, compound [I] is advantageously prepared by first producing the intermediate [V], [VI] or [VII] and then reacting it with a base. As the base are preferably used inorganic bases such as, for example, sodium hydrogen carbonate, potassium hydrogen carbonate, sodium carbonate, potassium carbonate, sodium hydroxide, potassium carbonate and calcium hydroxide. In some cases, however, organic bases such as ammonia, triethylamine, pyridine, lutidine, collidine and DBU (1,8-diazabicyclo[5.4.0]undec-7-ene) may also be employed. The base is usually used in an amount of 0.5–2.0 equivalents, preferably 1.0–1.5 equivalents, on the basis of compound [II]. An excess amount (2–10 equivalents) may also be used if the reaction is not hindered. The base may be used either as such or in solution in water for an inorganic base or in water or an appropriate solvent for an organic base. In the case where chlorine is used as the chlorinating agent, the base may be included from the beginning if the reaction is not hindered.

The allyl isothiocyanate derivatives [II], the starting materials in the present reaction are known substances, partly, or can be prepared by a method per se known. For example, the preparation can be effected by reacting a propene derivative (of the formula [VIII]) with a metal salt or ammonium salt of thiocyanic acid.

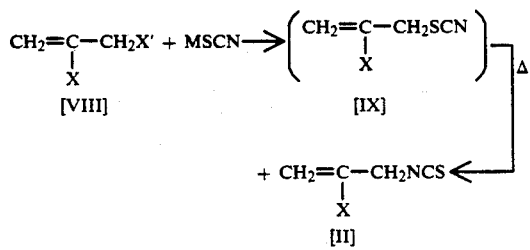

wherein X is as defined above, X' may be the same as or different from X and represents a leaving group as shown for X, and M represents a metal such as sodium, potassium, calcium, barium, zinc or copper or ammonium.

If the reaction is carried out at a low temperature (e.g. 80° C. or below), the first reaction product is usually a mixture of an allyl thiocyanate derivative (called compound [IX] hereinbelow) and an allyl isothiocyanate derivative [II] (compound [IX] only in some cases), but the compound [IX] can be rearranged by heating (e.g. 100° C. to 150° C.) to the desired product [II]. As the case may be, the compound [IX] can be converted into the desired product [II] by re-heating after transient isolation, or by heating in situ. Of course, the compound [II] may directly be produced by conducting the reaction at a high temperature (e.g. 100° C. to 150° C.) from the beginning. The compound [II] thus produced can be reacted with the chlorinating agent after isolation and/or purification, or without such treatments. It will be appreciated that the compound [I] can be produced via the compound [II] from the compound [VIII]. (B) 5-(Aminomethyl)-2-chlorothiazole (compound [III]) or salts thereof can be prepared by reacting an allyl isothiocyanate derivative [II] with a chlorinating agent to form 2-chloro-5-(chloromethyl)thiazole (compound [I]) and then reacting the resulting compound [I] with an aminating agent.

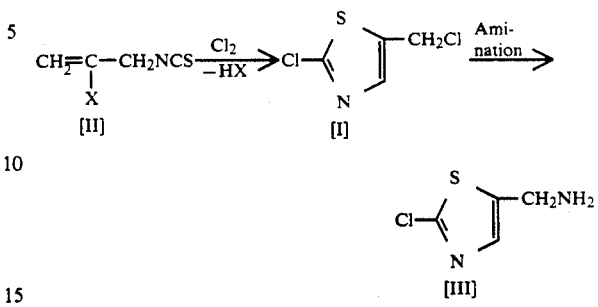

In the reaction, compound [I] is first prepared according to the conditions described for the method (A). The resulting compound [I] may be isolated and purified, or in some cases, it can be reacted with an aminating agent without isolation and purification. The aminating agent is preferably used in an amount of 0.8–1.5 equivalents on the basis of the compound [I] and may be used about 1.5–50 equivalents in some cases.

This step is often carried out in an appropriate solvent, though it may be done in the absence of solvent. As the solvent is used, for example, water, an alcohol such as methanol, ethanol, n-propanol or isopropanol, an aromatic hydrocarbon such as benzene, toluene or xylene, a halogenated hydrocarbon such as dichloromethane or chloroform, a saturated hydrocarbon such as hexane, heptane or cyclohexane, an ether such as diethyl ether, tetrahydrofuran (called THF for short hereinbelow) or dioxane, a nitrile such as acetonitrile, a sulfoxide such as dimethylsulfoxide (called DMSO for short hereinbelow), a carboxamide such as N,N-dimethylformamide (called DMF for short hereinbelow), or an ester such as ethyl acetate. These solvents may be used either alone, or as required, in combination of two or more in an appropriate ratio, for example, a ratio of 1:1–1:10. If the reaction mixture is not in homogeneous phase, the reaction may also be carried out in the presence of a phase transfer catalyst, for example, a quaternary ammonium salt such as triethylbenzylammonium chloride, tri-n-octylmethylammonium chloride, trimethyldecylammonium chloride or tetramethylammonium bromide, or a crown ether.

This step may also be promoted by the addition of 0.1–10 equivalents, preferably 1.0–3 equivalents of a base. As the base may be used an inorganic base such as sodium hydrogen carbonate, potassium hydrogen carbonate, sodium carbonate, potassium carbonate, sodium hydroxide, potassium hydroxide, calcium hydroxide, phenyllithium, butyllithium, sodium hydride, potassium hydride, sodium methoxide, sodium ethoxide, metallic sodium or metallic potassium, or an organic base such as triethylamine, tributylamine, N,N-dimethylaniline, pyridine, lutidine, collidine, 4-(dimethylamino)pyridine, or DBU. Said organic base itself may also be used as a solvent.

The reaction temperature and time in this step are usually −20° C.–150° C. and 10 min.–50 hours, preferably 0° C.–100° C. and 1 hour–20 hours, respectively.

It is necessary to remove the protective group which is known per se except for the case where ammonia (including aqueous ammonia) or an alkali metal salt thereof is used as the aminating agent. The removal can be effected in accordance with the procedures described, for example, in "Shin Jikken Kagaku Koza" (New Textbook Series of Chemical Experiments) (Maruzen), vol. 14-III, pp.1342-1349 and references cited therein.

More preferred reaction conditions with (i) aqueous ammonia, (ii) liquid ammonia, (iii) potassium or sodium phthalimide and (iv) hexamethylenetetramine as the aminating agent will be described below.

(i) With aqueous ammonia as the aminating agent

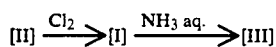

It is preferable to use aqueous ammonia in an amount about 5 to 50 equivalents to compound [I] as ammonia in order to avoid formation of polyalkylated products. The reaction solvent is preferably water, an alcohol or a nitrile as mentioned above, for example. The reaction temperatures and times are preferably 50° C.-100° C. and 30 min.-5 hours, respectively. In some cases, the reaction under high pressure (preferably from 1.1 to 10 atmospheres) can also reduce formation of polyalkylated products.

(ii) With liquid ammonia as the aminating agent

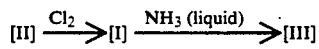

It is preferable to use an excess amount of ammonia (in an approximately 5 to 100-fold excess to the compound [I]) likewise in the reaction condition (i). Advantageously, the reaction is carried out under high pressure (preferably from 1.1 to 100 atmospheres). The reaction can be carried out in the presence of a solvent as mentioned above, though it may be done in the absence of a solvent. Examples of such solvents may include those mentioned above such as water, an alcohol, an aromatic hydrocarbon, a halogenated hydrocarbon, a saturated hydrocarbon, an ether, a nitrile, a sulfoxide, a carboxamide, or an ester. Reaction temperatures can be preferably in the range of from about −20° C. to +100° C. Reaction times can vary from about 30 minutes to about 40 hours.

(iii) With potassium or sodium phthalimide as the aminating agent

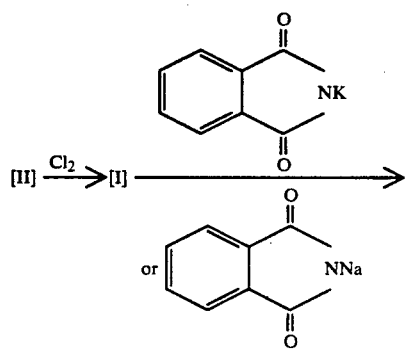

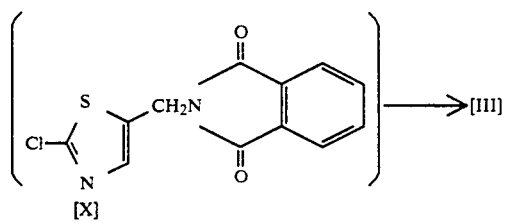

First, compound [I] and potassium or sodium phthalimide are reacted to produce an intermediate [X]. It is preferable to use potassium or sodium phthalimide in an amount of 1.0-1.5 equivalents on the basis of the compound [I]. The solvent may include those mentioned above such as alcohols, ethers, nitriles, ketones, sulfoxides and carboxylic acid amides, and DMF is particularly preferred. Using DMF as the solvent, the reaction temperature and time are preferably 10° C.-60° C. and 1 hour-10 hours, respectively.

Next, the intermediate [X] thus obtained is subjected to deprotection after or without isolation and purification. Hydrazinolysis is preferred for the deprotection though acid or alkaline hydrolysis is also applicable. Thus, the intermediate [X] and 1.0-1.2 equivalents of hydrazine (or hydrazine hydrate) on the basis of the intermediate [X] can be reacted in an appropriate solvent (for example, alcohols and nitriles as mentioned above) at 0° C.-100° C. for 1 hour-10 hours to give compound [III] or a salt thereof.

(iv) With hexamethylenetetramine as the aminating agent

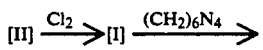

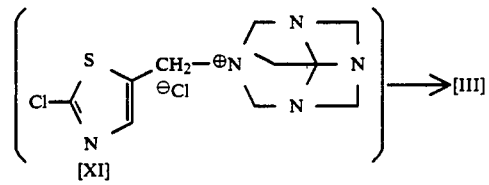

First, compound [I] and hexamethylenetetramine are reacted to give a quaternary ammonium salt intermediate [XI]. Hexamethylenetetramine is used preferably in an amount of 1.0-1.5 equivalents on the basis of the compound [I]. The solvent is preferably an alcohol, a halogenated hydrocarbon or a nitrile as mentioned above though a variety of solvents may be employed. The reaction temperature and time are preferably 20° C.-100° C. and 1-10 hours, respectively. The intermediate [XI] is preferably isolated at this stage but may be converted without isolation into compound [III]. Acid hydrolysis is usually employed for the hydrolysis of the intermediate [XI]. Thus, the intermediate [XI] is reacted preferably with 5-50 equivalents of an inorganic acid (such as hydrochloric, hydrobromic or sulfuric acid) on the basis of [XI]. The solvent is preferably water, an alcohol or a nitrile as mentioned above. When an organic solvent is used, it is preferably one containing about 5-50% of water. The reaction temperature and time are preferably 20°-100° C. and 20 min.-5 hours, respectively.

(C) 5-(Aminomethyl)-2-chlorothiazole [(II)] can be prepared by reacting 2-chloro-5-(chloromethyl)thiazole ([I]) with liquid ammonia or hexamethylenetetramine.

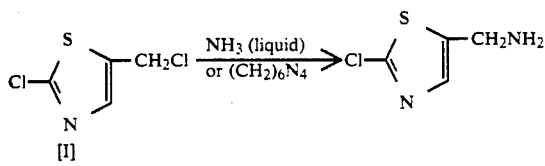

The reaction can proceed under the same reaction conditions as mentioned for the reaction of compound [I] obtained from compound [II] with an aminating agent in the latter part of the method (B). More preferably, the conditions under "(ii) with liquid ammonia as the aminating agent and (iii) with hexamethylenetetramine as the aminating agent" may be employed.

The compound [I] and compound [III] or salts thereof thus produced can be isolated by a known method such as concentration, concentration under reduced pressure, distillation, fractional distillation, solvent extraction, pH change, solvent change, chromatography, crystallization or recrystallization.

In the case where compound [III] is obtained in the above-mentioned process in free form, it can be converted by a conventional method into a salt, or vice versa.

As stated above, compound [I] and compound [III] or salts thereof are useful as a starting material for known insecticidal compounds. Moreover, it has been found that they are also useful as a starting material for novel insecticides. Thus, compound [I] prepared by the process according to the present invention is reacted with a compound represented by the formula

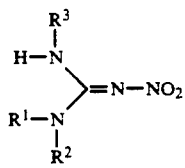

[XII]

wherein $R^1$, $R^2$ and $R^3$, which may be the same or different, respectively represent a hydrogen atom, a lower alkyl group or a lower carboxylic acyl group, or $R^1$ and $R^2$ taken together with the adjacent nitrogen atom represent a cyclic amino group or a salt thereof to afford compounds represented by the formula

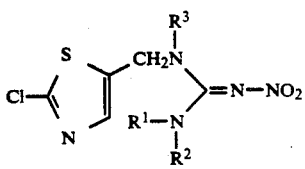

[XIII]

wherein each group has the same meaning as defined above or salts thereof.

It is preferable in the preparation of [XIII] to use about 0.8–1.5 equivalents of compound [I] on the basis of compound [XII]. However, a large excess of [I] may be used if the reaction is not hindered. The reaction may be carried out in the presence of a base and/or a cesium salt such as cesium chloride to promote reaction. As the base may be employed, for example, those which are referred to in the method (B) above. The base may be used in an amount of from 0.5 equivalent to a large excess, preferably about 0.8–1.5 equivalents on the basis of the compound [XII]. When an organic base is employed as the base it can also serve as a solvent. The cesium salt may be used in a catalytic amount (0.1 to 10 mol % to compound [XII]).

Usually, it is preferable to carry out the reaction in a solvent as mentioned in the method (B). If the reaction system is not in homogeneous phase a phase transfer catalyst may also be employed as stated in the method (B). The reaction temperature is usually −20° C.–150° C., preferably 0°–80° C. The reaction time is usually in the range of 10 min.–50 hours, preferably of 2 hours–20 hours. In addition, compound [III] or a salt thereof prepared according to the process of the invention is reacted with a compound represented by the formula

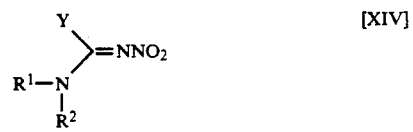

[XIV]

wherein $R^1$ and $R^2$ have the same meanings as defined above and Y represents a lower alkoxy group or a lower alkylthio group or a salt thereof to afford compounds represented by the formula

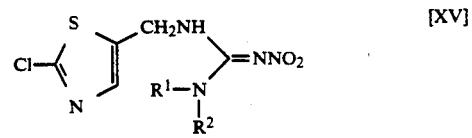

[XV]

wherein each group has the same meaning as defined above or salts thereof.

It is preferable to use about 0.8–2.0 equivalents of compound [III] or a salt thereof on the basis of the compound [XIV] or a salt thereof. However, about 2.0–20 equivalents may be employed if the reaction is not hindered.

The reaction is carried out usually in a solvent as mentioned in the method (B) though it may also be done in the absence of solvent. A phase transfer catalyst may also be employed as stated in the method (B) if the reaction system is not in homogeneous phase.

The reaction may also be promoted by adding a base and/or a metallic salt in an amount of 0.01–10 equivalents, preferably 0.1–3 equivalents on the basis of the compound [XIV]. As the base may be used, for example, those which are referred to in the method (B). When an organic base is used it can also serve as a solvent. As the metal salt may be employed, for example, copper salts such as copper chloride, bromide, acetate and sulfate and mercury salts such as mercury chloride, nitrate and acetate.

Temperature and time of the reaction are usually −50° C.–150° C. and 10 min.–50 hours, preferably −30° C.–100° C. and 30 min.–20 hours, respectively. As the lower alkyl group represented by $R^1$, $R^2$ and $R^3$ in the above formula is used, for example, methyl, ethyl, propyl or isopropyl, and as the lower carboxylic acyl, for example, formyl, acetyl or propionyl. As the cyclic amino group represented by $R^1$ and $R^2$ taken together with the adjacent nitrogen atom is used, for example, aziridino, azetidino, pyrrolidino, piperidino or morpholino. As the lower alkoxy group represented by Y is used, for example, methoxy, ethoxy, propoxy or isopropoxy, and as the lower alkylthio, for example, methylthio, ethylthio, propylthio or isopropylthio.

As the salt of compounds [XII], [XIII], [XIV] and [XV] are used, for example, those which are mentioned above for compound [III].

As described above, use of the process according to the invention enables production of compounds [XIII] or salts thereof from compound [II] via compound [I], as well as of compounds [XV] or salts thereof from compound [II] via compound [I] and compound [III] or a salt thereof, or from compound [I] via compound [III] or a salt thereof.

Compounds [XIII] or salts thereof and compounds [XV] or salts thereof thus prepared possess a high insecticidal activity.

EXAMPLES

The invention will be described in more detail below with reference to examples and reference examples. However, the invention is not intended to be limited to these examples.

Elution of the column chromatography in the examples and the reference examples were made under observation with TLC (thin layer chromatography). There were employed in the TLC observation Kieselgel 60F$_{254}$ (70–230 mesh, Merck) as the TLC plate, a solvent used as the eluent in the chromatography as the developing solvent and a UV detector as the detecting method. As the silica gel for column chromatography was used Kieselgel 60 (70–230 mesh, Merck). The NMR represents a proton NMR using tetramethylsilane as the internal standard, being measured on VARIAN EM390 (90 MHz) and being indicated in terms of all δ value in ppm. The figures in ( ) for a mixed solvent used as the developing solvent indicate volume ratio of the solvents in the mixture.

Abbreviations in the examples and the reference examples have the following meanings.

Me: methyl, Et: ethyl, s: singlet, br: broad, d: doublet, t: triplet, q: quartet, m: multiplet, dd: doublet of doublet, J: coupling constant, Hz: herz, CDCl$_3$: deuterochloroform, DMSO-d$_6$: deutero-DMSO, %: % by weight, mp: melting point, bp: boiling point and room temperature means a temperature of ca. 15°–25° C.

The foregoing is merely illustrative of the invention and is not intended to limit the invention to the disclosed compounds and procedures. Variations and changes which are obvious to one skilled in the art are intended to be within the scope and nature of the invention.

EXAMPLE 1

Into a mixture of 13.4 g of 2-chloroallyl isothiocyanate and 10 ml of chloroform was introduced gaseous chlorine under cooling with ice (inner temperature of 10° C. or below) over one hour and 40 min. Weight of the gaseous chlorine absorbed was 7.71 g. At this stage, the products, according to NMR, were estimated as 2-aza-1,4-dichloro-1,4-pentadienesulfenyl chloride $$CH_3=C-CH_2N=C-SCl$$
$$\phantom{CH_3=}\overset{|}{Cl}\phantom{-CH_2N=}\overset{|}{Cl}$$

(NMR(CDCl$_3$): 4.33(2H, m), 5.38(1H, m), 5.53(1H, m))

and 2,5-dichloro-5-(chloromethyl)-2-thiazoline

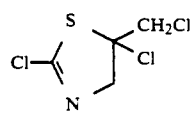

(NMR(CDCl$_3$): 4.08(2H, m), 4.58(2H, m))

Removal of the bath raised the temperature, and a water bath was applied to maintain the inner temperature at 40° C. or below. After 4 hours exothermic reaction did not occur, when the bath was removed. 2-Chloro-5-(chloromethyl)thiazole was yielded as the main product at this stage. The chloroform was removed by distillation followed by distillation under reduced pressure to give 13.3 g of 2-chloro-5-(chloromethyl)thiazole in a yield of 73%. Bp 108°–110° C./18 mmHg, mp ca. 30° C. NMR (CDCl$_3$): 4.72(2H, s), 7.51 (1H, s).

EXAMPLE 2

To a mixture of 50 g of 2-chloroallyl isothiocyanate and 50 ml of chloroform was added 60.1 g of sulfuryl chloride over one hour and 30 min, maintaining the inner temperature at 30° C. or below in water bath. The bath was removed, and the mixture was allowed to react at room temperature for additional 2 hours and 30 min. The inner temperature reached 36° C. at maximum due to slow exothermic reaction during that period of time. The solvent and the excess of the sulfuryl chloride were removed by distillation. The residue was dissolved in 400 ml of dichloromethane, and the solution washed with aqueous sodium bicarbonate and water and dried over magnesium sulfate and then concentrated. The residue was subjected to distillation under reduced pressure to give 51.7 g of 2-chloro-5-(chloromethyl)-thiazole. Yield: 82%, purity: > 90%, bp: 110° C./20 mmHg.

EXAMPLE 3

To 11.6 g of 2-chloroallyl isothiocyanate was dropwise added 103 ml of a 0.834M carbon tetrachloride solution of chlorine over one hour and 30 min. while cooling with ice (inner temperature of 5° C. or below). After stirring was continued for 1 hour under cooling with ice and for 4 hours at room temperature, it was estimated according to NMR that the product was only 2-aza-1,4-dichloro-1,4-pentadienesulfenyl chloride with a small amount of starting material. Distillation of the carbon tetrachloride under normal pressure from the reaction solution afforded 2-chloro-5-(chloromethyl)-thiazole as the main product.

EXAMPLE 4

To 1.00 g of sulfuryl chloride was added 0.43 g of 2-chloroallyl isothiocyanate over 3 min., and the mixture stirred at room temperature for 30 min. To the reaction solution was added 10 ml of carbon tetrachloride, and the reaction mixture concentrated under reduced pressure at a temperature of 10° C. or below. The main product at this stage was estimated as 2,5-dichloro-5-(chloromethyl)-2-thiazoline, and heating at 60° C. for 30 min. yielded 2-chloro-5-(chloromethyl)-thiazole as the main product.

EXAMPLE 5

To 0.50 g of sulfuryl chloride was dropwise added 0.22 g of 2-chloroallyl isothiocyanate over 3 min. while cooling with ice. Stirring was continued under cooling with ice for 1 additional hour followed by addition of 10 ml of chloroform. The reaction mixture was concentrated under reduced pressure at a temperature of 20° C. or below. The main product at this stage was estimated as 2,5-dichloro-5-(chloromethyl)-2-thiazoline, and further concentration at 40° C.–60° C. converted the main product to the substance which was estimated as 2-chloro-5-(chloromethyl)thiazole hydrochloride or 2,2-dichloro-5-(chloromethyl)-4-thiazoline.

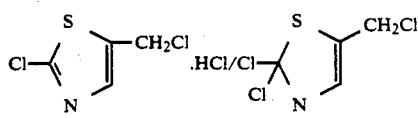

(NMR(CDCl$_3$): 4.79(2H, s), 7.70(1H, s))

Addition of chloroform to this product followed by addition of diluted aqueous ammonia or aqueous sodium bicarbonate and stirring at 20° C. or below yielded 2-chloro-5-(chloromethyl)thiazole.

EXAMPLE 6

A mixture of 1.0 g of 2-chloro-5-(chloromethyl)-thiazole obtained by the procedures in Example 2, 4 ml of 25% aqueous ammonia and 6 ml of acetonitrile was placed in a stainless steel autoclave and reacted at 80° C. for 2 hours. After cooling, 0.6 ml of a 10N aqueous solution of sodium hydroxide and 12 ml of ethanol were added, and the mixture stirred at room temperature for 30 min. The reaction mixture was concentrated followed by addition of 20 ml of dichloromethane and dried over anhydrous magnesium sulfate. Insoluble materials were separated by filtration and the filtrate was then concentrated. The concentrate was purified by column chromatography (eluted with dichloromethane-methanol 10:1) to afford 0.49 g of 5-(aminomethyl)-2-chlorothiazole as yellow liquid. NMR (CDCl$_3$): 1.66(2H, s), 4.02(2H, s), 7.36 (1H, s).

EXAMPLE 7

A mixture of 0.50 g of 2-chloro-5-(chloromethyl)-thiazole, 4 ml of 25% aqueous ammonia and 6 ml of acetonitrile was heated under reflux for 30 min. followed by supplement of 8 ml of 25% aqueous ammonia. The mixture was heated under reflux for 30 additional min. After-treatment in the same way as in Example 6 yielded 0.22 g of 5-(aminomethyl)-2-chlorothiazole.

EXAMPLE 8

To a mixture of 27.5 g of hexamethylenetetramine and 150 ml of chloroform was dropwise added 30.0 g of 2-chloro-5-(chloromethyl)thiazole over 30 min. while heating under reflux. The mixture was heated under reflux with stirring for 3 hours and then allowed to stand overnight. Crystals thus formed were separated by filtration and washed with 100 ml of chloroform. Combined filtrate and washing were concentrated to 100 ml. Crystals formed after being allowed to stand for half a day were separated by filtration and washed with 20 ml of chloroform. Combined filtrate and washing were treated two more times in the same way as above. There was obtained a total of 55.0 g (yield, 99.7%) of a quaternary ammonium salt.

A mixture of 32.5 g of the quaternary ammonium salt, 104 g of 36% hydrochloric acid, 97.5 ml of water and 325 ml of ethanol was stirred at 70° C. for one hour and then allowed to stand overnight. Solids then formed were separated by filtration, and the filtrate was concentrated to about a half of the original volume. Solids formed were again separated by filtration, and the filtrate was concentrated to dryness. To the residue was added 100 ml of acetone, and insoluble materials collected by filtration. To the filtrate was added 250 ml of water, and pH adjusted with 6N aqueous sodium hydroxide to 13. The mixture was extracted three times with dichloromethane, and the dichloromethane layers washed with saturated aqueous sodium chloride, dried over anhydrous potassium carbonate and concentrated. There was obtained 14.3 g of crude 5-(aminomethyl)-2-chlorothiazole, which was purified by distillation under reduced pressure to give 10.5 g of pure products, bp: 85° C./10.5 mmHg.

EXAMPLE 9

A mixture of the quaternary ammonium salt (77.1 g) obtained by the procedure in the first half of Example 8, ethanol (80 ml), water (160 ml), and 12N hydrochloric acid (200 ml) was stirred at an internal temperature ranging from 70° C. to 75° C. for 2 hours and then insoluble materials were separated by filtration after cooling. The filtrate was concentrated to about 300 ml and the precipitated material again separated by filtration. The filtrate was concentrated and 300 ml of water was added to the concentrate followed by further concentration. The residue was washed with acetone, dissolved in 150 ml of water and pH adjusted with 6N aqueous sodium hydroxide to 13 under cooling with ice. The mixture was extracted three times with dichloromethane, dried over anhydrous magnesium sulfate, and concentrated to yield 28.1 g (75.6%) of 5-(aminomethyl)-2-chlorothiazole. A portion (21.2 g) of the product was distilled under reduced pressure to give 17.2 g of pure product, bp: 71°-2° C./0.7 mmHg.

EXAMPLE 10

To a mixture of potassium phthalimide (10.4 g) and dry DMF (100 ml) was dropwise added a solution of 2-chloro-5-(chloromethyl)thiazole (9.0 g) obtained in the same manner as in Example 2, in 10 ml of DMF in an oil bath at 20° C. over 15 min. After completion of the addition stirring was continued at 60° C. for 45 min. followed by separation of insoluble materials by filtration on celite. The filtrate was concentrated under reduced pressure. To the residue was added 100 ml of dichloromethane again followed by separation of insoluble materials by filtration and concentration of the filtrate. The residue was purified by column chromatography (eluted with dichloromethane-ethyl acetate 20:1) to give 12.0 g of N-(2-chloro-5-thiazolylmethyl)phthalimide, mp 108°-109° C.

To a mixture of 12.0 g of N-(2-chloro-5-thiazolylmethyl)phthalimide and 200 ml of ethanol was dropwise added 3.2 g of hydrazine hydrate over 5 min. After completion of the addition the mixture was heated under reflux for one hour and cooled. White solid then formed was separated by filtration, and concentration of the filtrate afforded 4.9 g of almost pure 5-(aminomethyl)-2-chlorothiazole.

EXAMPLE 11

Into an autoclave under cooling in an acetone-dry ice bath was placed 20 ml of liquid ammonia and a mixture of 2-chloro-5-(chloromethyl)thiazole (3.36 g) and toluene (10 ml) was added to the autoclave before sealing. The mixture was allowed to set at a bath temperature of −30° C. followed by elevating to 0° C. under stirring over 2.5 hours. Then stirring was continued for 7 hours in an ice bath and for 16 hours at room temperature followed by ambient pressure. The reaction mixture was transferred into 10 ml of 6N aqueous sodium hydroxide, and extracted two times with dichloromethane (100 ml and 50 ml). The organic layer was concentrated and then purified by column chromatography (eluted with dichloromethane-methanol 10:1) to yield 2.20 g (74.0%) of 5-(aminomethyl)-2-chlorothiazole.

COMPARATIVE EXPERIMENT

Preparation of 2-chloro-5-(chloromethyl)thiazole by the method described in Japanese Patent Application Laid Open No. 83079/1988

Sulfuryl chloride (1500 g) was heated to 50° C. and 250 ml of allyl isothiocyanate was added dropwise over 5 hours. Thereafter, the mixture was heated at 80° C. for additional 2 hours. After removal of sulfuryl chloride by distillation, the reaction mixture was distilled under reduced pressure (20 mmHg). A distilled fraction at bp 90°-110° C. was collected (295 g, purity: 28% estimated by gas chromatography). The fraction was further subjected to fractional distillation (Widmer fractional distilling column) to collect a distillate at bp 63°-68° C./1.3 mmHg (118 g, purity: 50% estimated by gas chromatography). The distillate was purified by column chromatography (eluted with hexane-ether=8:1) to yield 46 g of pure 2-chloro-5-(chloromethyl)thiazole.

REFERENCE EXAMPLE 1

Synthesis of 2-chloroallyl isothiocyanate

A mixture of 325.9 g of 2,3-dichloro-1-propene, 261.9 g of sodium thiocyanate and 1.5L of acetonirile was heated under reflux for 3 hours and 30 min. Then, insoluble materials were separated by filtration, and the filtrate concentrated. To the residue was added 200 ml of dichloromethane again followed by separation of insoluble materials and concentration. The residue was stirred in an oil bath at 140° C. for 1 hour and distilled under reduced pressure. There was obtained 339.5 g of 2-chloroallyl isothiocyanate, bp 73°-76° C./18 mmHg.

REFERENCE EXAMPLE 2

To a mixture of 13.0 g of N,N-dimethyl-N'-nitroguanidine, 5.90 g of powdery sodium hydroxide and 200 ml of dry DMF was dropwise added a solution of 2-chloro-5-(chloromethyl)thiazole in 15 ml of DMF over 2 hours while cooling with ice. The bath was removed, and stirring continued at room temperature for 13 hours followed by removal of the DMF by distillation under reduced pressure. To the residue was added 200 ml of acetonitrile followed by separation of insoluble materials by filtration on celite. The filtrate was purified by column chromatography (eluted with dichloromethane-acetonitrile 2:1-1:2). There was obtained 6.45 g of 1-(2-chloro-5-thiazolylmethyl)-3,3-dimethyl-2-nitroguanidine (reference compound No. 1), mp 155°-160° C. Crystallization from ethanol raised mp to 165.5°-166.5° C. NMR (DMSO-$d_6$): 2.96(6H, s), 4.50(2H, d, J=5.8 Hz), 7.56(1H, s), 8.53(1H, br t, J=5.8 Hz).

Similarly, the following compounds were obtained: 1-(2-chloro-5-thiazolymethyl)-3-ethyl-3-methyl-2-nitroguanidine (reference compound No. 2, mp 165°-167° C.), 1-(2-chloro-5-thiazolylmethyl)-3,3-diethyl-2-nitroguanidine (reference compound No. 3, syrup, NMR (CDCl$_3$): 1.23(6H, t, J=7 Hz), 3.46(4H, q, J=7.2 Hz), 4.60(2H, br s), 7.44(1H, s), 8.30(1H, br s)), 1-[1-(2-chloro-5-thiazolylmethyl)-2-nitroamidino]pyrrolidine (reference compound No. 4, mp 185°-188° C.).

REFERENCE EXAMPLE 3

To a mixture of 5.0 g of S-methyl-N-nitroisothiourea and 25 ml of pyridine was dropwise added 11.3 of acetic anhydride at room temperature over 10 min. After completion of the addition the mixture was stirred at room temperature for 5 hours, and the reaction mixture concentrated. The residue was poured onto 50 ml of 2N hydrochloric acid, and crystals then formed collected by filtration and dried. There was obtained 5.1 g of N-acetyl-S-methyl-N'-nitroisothiourea as white crystals, mp 109°-110° C.

To a mixture of 0.22 g of N-acetyl-S-methyl-N'-nitroisothiourea and 5 ml of acetonitrile was dropwise added 0.2 g of 5-(aminomethyl)-2-chlorothiazole at −2° C. Stirring was continued at the same temperature for additional 1 hour, and then the reaction mixture concentrated. The residue solidified was recrystallized from ethanol to give 0.31 g of N-actyl-N'-(2-chloro-5-thiazolylmethyl)-N''-nitroguanidine (reference compound No. 5), mp 132°-133° C. NMR (CDCl$_3$): 2.33(3H, s), 4.68(2H, d, J=6 Hz), 7.50(1H, s), 9.60(1H, br), 11.85(1H, br).

REFERENCE EXAMPLE 4

A mixture of 6.82 g of 5-(aminomethyl)-2-chlorothiazole, 7.26 g of 1,2-dimethyl-3-nitroisothiourea, 6.72 g of anhydrous potassium carbonate, 4.81 g of cuprous chloride and 150 ml of acetonitrile was heated under reflux for 1 houf. Insoluble materials were separated by filtration while hot, and the filtrate concentrated. The concentrate was purified by column chromatography (eluted with dichloromethane-methanol 10:1). There was obtained 7.33 g of 1-(2-chloro-5-thiazolylmethyl)-3-methyl-2-nitroguanidine (reference compound No. 6), mp 172°-174° C. (recrystallized from acetonitrile). NMR(DMSO-$d_6$):2.83(3H, d, J=5 Hz), 4.53(2H, d, J=5 Hz), 7.61(1H, s), 8.12(1H, br s), 9.00(1H, br s).

REFERENCE EXAMPLE 5

To a mixture of 0.50 g of 1,2-dimethyl-3-nitroisothiourea and 10 ml of pyridine was dropwise added 1.03 g of acetic anhydride at room temperature. The mixture was stirred at room temperature for 1 hour, and then poured onto 150 ml of 2N hydrochloric acid followed by extraction with 100 ml of chloroform. The chloroform layer was washed with 50 ml of 2N hydrochloric acid and then concentrated to give 0.60 g of 1-acetyl-1,2-dimethyl-3-nitroisothiourea as pale yellow liquid. NMR (CDCl$_3$):2.23(3H, s), 2.52(3H, s), 3.17(3H, s).

To a mixture of 0.514 g of 1-acetyl-1,2-dimethyl-3-nitroisothiourea and 5 ml of toluene was dropwise added a mixture of 0.400 g of 5-(aminomethyl)-2-chlorothiazole, 10 ml of toluene and 2 ml of ether under cooling with ice over 10 min. The mixture was stirred under cooling with ice for 2 hours, and white crystals formed were collected by filtration to give 0.230 g of N-acetyl-N'-(2-chloro-5-thiazolymethyl)-N-methyl-N''-nitroguanidine (reference compound No. 7), mp 105°-108° C. NMR (CDCl$_3$):2.11(3H, s), 3.08(3H, s), 4.57(2H, s), 7.53(1H, s), 9.35(1H, br s).

REFERENCE EXAMPLE 6

To a mixture of 1,2-dimethyl-3-nitroisothiourea (2.93 g), potassium carbonate (4.07 g), and acetonitrile (60 ml) was added acetic anhydride (2.53 g) at room temperature and the mixture was stirred for 3 hour at this temperature. Insoluble materials were removed by filtration and the filtrate was concentrated. Chloroform (100 ml) was added to the residue and the mixture was washed with water twice. The chloroform layer was dried over anhydrous magnesium sulfate and concentrated to give 3.48 g of 1-acetyl-1,2-dimethyl-3-nitroisothiourea.

To a solution of 1-acetyl-1,2-dimethyl-3-nitroisothiourea (3.41 g) in ethyl acetate (20 ml) was dropwise added a solution of 5-(aminomethyl)-2-chlorothiazole (2.65 g) in ethyl acetate (4 ml) at −25° C. for 15 min. and stirring was continued for further 30 min. at −25° C. Then the mixture was allowed to warm to 20° C. for 5 min. and concentrated to about 8 ml. Diisopropyl ether (4 ml) was added to the residue and the precipitates were collected by filtration to give 4.22 g of N acetyl N'-(2-chloro-5-thiazolymethyl)-N-methyl-N''-nitroguanidine (reference compound No. 7), mp 105°-107° C. (recrystallized from ethyl acetate).

REFERENCE TEST EXAMPLE

Effect against brown planthopper (*Nilaparvata lugens*)

Leaf and stem of the 2nd-leaf-stage seedlings of rice grown in a nursery box were sprayed by means of a spray gun with 500 ppm of a test compound (the compound number as indicated in the examples referred to) prepared by dissolving 5 mg of the compound in 0.5 ml of acetone containing Tween 20 ® and diluting with a 3000-fold diluted solution of Dyne ® (a spreader manufactured by Takeda Chemical Industries) to the predetermined concentration (500 ppm) at a rate of 10 ml of the drug solution per paper pot. Water was placed in a test tube at the bottom, in which 10 larvae at the third instar of brown planthopper were released, and the test tube was closed with an aluminum stopper and placed in an incubator adjusted to 25° C. Dead larvae were counted seven days after release. It was found that all of the compounds Nos. 1-7 exhibited 100% mortality.

As many widely different embodiments of this invention may be made without departing from the spirit and scope thereof, it is to be understood that this invention is not limited to the specific embodiments thereof except as defined in the appended claims.

The following references, which referred to for their disclosures at various points in this application, are incorporated herein by reference.
1. European Patent Application Laid Open No. 192,060.
2. Japanese Patent Application Laid Open No. 171/1990.
3. Japanese Patent Application Laid Open No. 83079/1988.
4. Japanese Patent Application Laid Open No. 83979/1988.
5. Shin Jikken Kagaku Koza, New Textbook Series of Chemical Experiments, Maruzen K. K., vol. 14-III, pp. 1342-1349.

What is claimed is:

1. A process for preparing 2-chloro-5-(chloromethyl)thiazole represented by

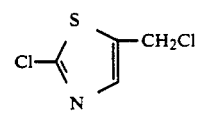

[I]

which comprises reacting an allyl isothiocyanate derivative represented by the formula

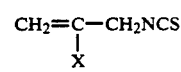

[II]

wherein X represents a leaving group selected from the group consisting of halogen; C$_{1-4}$ alkylsulfonyloxy unsubstituted or substituted by 1 to 3 halogen atoms which may be the same or different; C$_{6-10}$ arylsulfonyloxy unsubstituted or substituted by 1 to 4 substituents, which may be the same or different, selected from the group consisting of lower alkyl and halogen atoms; and C$_{1-6}$ acyloxy unsubstituted or substituted by 1 to 3 halogen atoms which may be the same or different; with a chlorinating agent.

2. A process according to claim 1 wherein X in the formula [II] is a chlorine atom.

3. A process according to claim 1 wherein the chlorinating agent is chlorine or sulfuryl chloride.

4. A process according to claim 1, wherein X represents a leaving group selected from the group consisting of fluorine, chlorine, bromine, iodine, methanesulfonyloxy, ethanesulfonyloxy, butanesulfonyloxy, trifluoromethanesulfonyloxy, benzenesulfonyloxy, p-toluenesulfonyloxy, p-bromobenzenesulfonyloxy, mesitylenesulfonyloxy, acetyloxy, propionyloxy, trifluoroacetyloxy, and benzoyloxy.

5. A process for preparing 5-(aminomethyl)-2-chlorothiazole

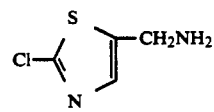

[III]

or salts thereof which comprises reacting an allyl isothiocyanate derivative represented by the formula

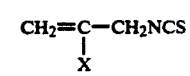

[II]

wherein X represents a leaving group with a chlorinating agent to produce 2-chloro-5-(chloromethyl)thiazole represented by

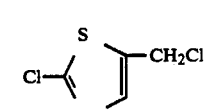

[I]

and then reacting the resulting compound with an aminating agent.

6. A process according to claim 5 wherein X in the formula [II] is a chlorine atom.

7. A process according to claim 5 wherein the chlorinating agent is chlorine or sulfuryl chloride.

8. A process according to claim 5, wherein the aminating agent is ammonia.

9. A process according to claim 5, wherein the aminating agent is potassium phthalimide or sodium phthalimide.

10. A process according to claim 5, wherein the aminating agent is hexamethylenetetramine.

11. A process according to claim 5, wherein the aminating agent is liquid ammonia.

* * * * *